United States Patent [19]

Christensen

[11] Plant 4,659

[45] Mar. 3, 1981

[54] ROSE PLANT

[75] Inventor: Jack E. Christensen, Ontario, Calif.

[73] Assignee: Armstrong Nurseries, Inc., Ontario, Calif.

[21] Appl. No.: 87,810

[22] Filed: Oct. 24, 1979

[51] Int. Cl.[3] ..... A01H 5/00
[52] U.S. Cl. ..... Plt./7
[58] Field of Search ..... Plt./7

*Primary Examiner*—Robert E. Bagwill

*Attorney, Agent, or Firm*—William H. Elliott, Jr.; Andrew R. Klein

[57] ABSTRACT

A rose plant of the hybrid miniature class, being a dwarf bush outdoor seedling chiefly used for garden decoration. Flowers are large, for roses of this class, ranging from 1½ to 2 inches, and comprising 18 to 28 petals with 1 to 7 petaloids. Color effect is of orange-apricot and yellow, the blooms having a slight fragrance and being borne on strong stems of average or better length. The growth habit is very vigorous, the plant being much branched and bushy.

1 Drawing Figure

1

This invention relates to a new class of hybrid miniature rose. The plant is an outdoor seedling of the dwarf bush type, cultivated for garden decoration. Its hardiness is untested. It was propagated by Jack E. Christensen in Ontario, Calif., having as its seed parent "Gingersnap" (U.S. Plant Pat. 4,330) and, as its pollen parent, "Magic Carrousel" (U.S. Plant Pat. 3,601). It holds its distinguishing characteristics through succeeding propagations by cuttings and by budding.

The new variety bears its flowers usually singly, although sometimes two to three to a stem, in irregular clusters on stems which are strong and medium to long, for miniature roses. The plant blooms very freely outdoors, and nearly continuously during the growing season. It has a slight fragrance.

This new miniature rose cultivar may be distinguished from its seed parent, Gingersnap, by the following combination of characteristics:

Gingersnap bears flowers of relatively uniform bright orange coloration, whereas the new rose bears flowers of orange-apricot and yellow coloration essentially as described herein.

Gingersnap has significantly larger blooms of 3¼ inches to 4 inches in diameter than the new cultivar, which has blooms of 1½ inches to 2 inches in diameter.

The new cultivar is classed as a hybrid miniature rose, whereas Gingersnap is in the hybrid floribunda classification.

This new miniature rose cultivar may be distinguished from its pollen parent, Magic Carrousel, by the following combination of characteristics:

Magic Carrousel bears flowers of white and red coloration, whereas the new rose bears flowers of orange and yellow coloration essentially as described herein.

The new cultivar has a significantly more upright plant habit than does Magic Carrousel, although both are miniature.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

2

BUD

The peduncle is average length for miniature roses, of heavy caliper and erect, usually smooth and with few stipitate glands. The color is between Strong Yellow Green, 5GY6/8, and Strong Yellow Green, 2.5GY6/8.

Before the calyx breaks, the bud is medium to large in size for miniature roses. It is moderately long, pointed and ovoid in form, with slight glandular bloom on the surface of the bud, and usually with slender foliaceous parts extending beyond the tip of the bud equal to one-half of its length.

As the calyx breaks, the color hues vary from as light as Strong Reddish Orange, 10R6/12, to as dark as Strong Reddish Orange, 7.5R5/13.

The inner surface of the sepals is lined with a fine tomentum; margins are lined with hairs.

As the first petal opens, the bud is average to large in size, for miniature roses, medium-length, and pointed-ovoid in form. The color on the outside of the petal is between Brilliant Yellow, 2.5Y9/9, and Vivid Yellow, 2.5Y8/12, over a majority of the petal, while the edge of the petal approaches Strong Orange, 5YR7/11. The inside of the petal has a zone near Vivid Yellow, 5Y8/12, at the base, while the remainder of the petal is between Strong Reddish Orange, 10R5/11, and Strong Reddish Orange, 7.5R5/13. The bud opens up well and is not prevented from opening by cold, hot, wet or dry weather.

BLOOM

The size of the bloom when fully open is large for miniature roses, being from 1½ inches to 2 inches. The petalage is double, with from 18 to 28 petals, plus from 1 to 7 petaloids arranged regularly. The bloom is full and high centered at first, becoming open to cupped, the petals remaining at first somewhat tightly cupped with tips rolled outward, becoming later at maturity more loosely cupped, with tips reflexed outward.

The petals are of medium thickness and moderately leathery, with the inside being slightly satiny and the outside being slightly shiny to satiny. The outside petals are round to obovate, with slightly mucronate apex. Intermediate petals are broadly obovate, with slightly mucronate apex. Inside petals are obovate, also with slightly mucronate apex. The colors may be modified by being dotted, shaded and/or washed or tinted with other colors.

The paragraph immediately following describes color values observed in a flower newly opened in the month of June. The plant had been grown outdoors, in Ontario, Calif.

The same coloration was noted in all petals, namely outside, intermediate and inner petals. The majority of the outer surface of the petal from the base up was near Brilliant Yellow, 2.5Y9/9, while the petal edge approached Light Orange, 5YR8/7. The inner surface of the petal showed a basal zone between Brilliant Yellow, 5Y9/9, and Vivid Yellow, 5Y8/12, while the rest of the petal varied between Light Orange, 5YR8/7, and Strong Reddish Orange, 10R6/12.

The paragraph immediately following describes the color values observed in a bloom which had been open for three days, outdoors, in the month of June. The plant had been grown outdoors, in Ontario, Calif.

Outer and inner surfaces of both outside and inside petals were the same in coloration. The outer surface showed a basal zone near Brilliant Greenish Yellow, 7.5Y9/8, with the petal edge being lightly washed with near Light Orange, 2.5YR8/6. The inner surface was the same except that the very edge of the petal can intensify to near Deep Pink, 2.5R6/11.

In the general color effect the hues of the newly opened flower vary from near Brilliant Yellow, 2.5Y9/9, to near Strong Orange, 2.5YR7/10. The bloom after being three days open gives a general color effect of hues varying from near Brilliant Yellow, 2.5Y9/9, to near Strong Yellowish Pink, 7.5R7/9. The petals persist, the color of the petal edge intensifying to near Strong Red, 2.5R5/12. The petals are not particularly affected by cold, hot, wet or dry weather.

The flower on the bush in the garden persists for from 3 to 5 days in the month of June, in the locality named. Cut roses grown outdoors last 3 to 5 days in the month of June.

REPRODUCTIVE ORGANS

There are from an average number to many stamens, for miniature roses, arranged regularly about the pistils, a few being tucked in the calyx.

The filaments are short to medium-length, and near Vivid Yellow, 2.5Y8/12, in color. Most are with anthers.

The anthers are medium size to large, all opening approximately at once. Before dehiscence, the outer edge is near Vivid Yellow, 2.5Y8/12, in color, while the remainder is near Brilliant Greenish Yellow, 7.5Y9/8.

Pollen is moderate in amount and near Vivid Yellow, 2.5Y8/12, in color.

The pistils are average in number, there being approximately 35.

The styles are even, average length for miniature roses, from average to heavy in caliper, and loosely bunched. The color is near Brilliant Greenish Yellow, 7.5Y9/8.

The stigma is near Brilliant Greenish Yellow, 10Y9/9, in color.

The ovaries are mostly all enclosed in the calyx.

Immature hips were long, oblong in shape, and with a color near Strong Yellow Green, 2.5GY7/10.

Sepals are permanent, long, straight and curled. On the inside they were near Strong Yellow Green, 5GY6/8, in color, while the outside was a color near Brilliant Yellow Green, 5GY8/8, with a gray bloom.

There are few seeds, from 1 to 4 in number, and usually small to medium size.

FOLIAGE

The compound leaves usually comprise from 3 to 5 leaflets. They are sparse to normal, medium size for miniature roses, and moderately heavy to somewhat leathery and glossy. The leaflets are ovate in shape, with apex acute to acuminate, base acute, and margin doubly serrate. Some margins curl toward the leaf underside.

The mature foliage displays upon its upper surface a color which is between Grayish Olive Green, 7.5GY3/2, and Moderate Olive Green, 5GY4/3. The under surface is between gray and Moderate Olive Green, 5GY4/3.

The young foliage on its upper surface is near Moderate Olive Green, 5GY4/3, in color, but washed heavily with near Dark Red, 2.5R3/7. Its under surface is near Strong Yellow Green, 5GY6/8, in color, washed with near Dark Red, 2.5R3/7.

The rachis is average in size, grooved on its upper side, with a few stipitate glands on the edges. The under side is moderately prickly.

The stipules are medium-length to long, medium-width, with medium-length to long points turning out at an angle of more than 45°.

The plant displays a more than average resistance to mildew, when compared with other varieties now in commerce under comparable conditions, when grown at Ontario, Calif.

GROWTH

The plant is a bushy dwarf, upright in habit and much branched. It displays a very vigorous growth. The canes are medium to heavy in caliper, for miniature roses.

The main stems are near Moderate Olive, 10Y4/3, in color. They bear several medium-length large prickles, which are almost straight to hooked slightly downward, with medium-length, moderately broad base. Their color is between gray and Strong Brown, 5YR4/5. There are several small prickles which are the same coloration as the large prickles. There are no hairs.

The branches are between Strong Yellow Green, 2.5GY6/8, and Moderate Olive Green, 2.5GY4/3, in color. They bear several large prickles which are medium-length, almost straight to hooked slightly downward, with medium-length, moderately broad base. These are between Strong Brown, 5YR4/5, and Moderate Brown, 7.5YR4/5, in color. There are several small prickles which are the same coloration as the large prickles. There are no hairs.

New shoots are near Moderate Yellow Green, 2.5GY5/5, in color, but are washed with Dark Red, 2.5R3/7. They bear from few to several large prickles, which are medium-length, almost straight, and with medium-length narrow base. These are near Strong Reddish Orange, 7.5R5/13, in color. There are few small prickles, and these are the same coloration as the large prickles. There are a few hairs which are also the same coloration as the large prickles.

I claim:

1. An outdoor bush rose plant of the hybrid miniature class, substantially as shown and described, being a dwarf seedling mainly used for garden decoration, said plant being much branched and bushy and bearing its blooms usually singly on strong, medium-length to long stems, said blooms being from about 1.5 to 2.0 inches in diameter, having 18 to 28 petals and 1 to 7 petaloids, the overall color effect of the newly opened flower being orange-apricot and yellow.

* * * * *

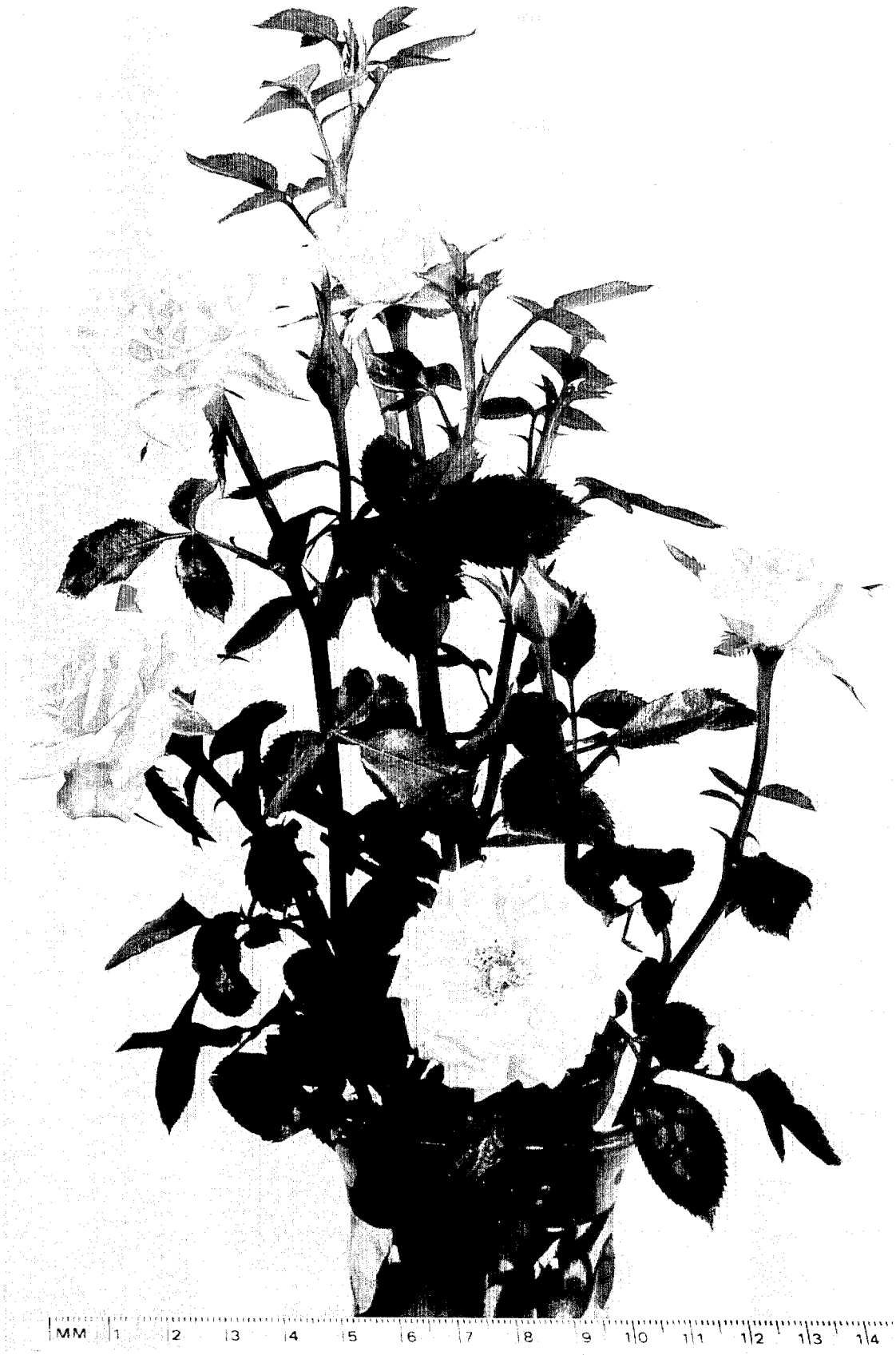
MM 1 2 3 4 5 6 7 8 9 10 11 12 13 14